US007867969B2

(12) United States Patent
Decoster et al.

(10) Patent No.: US 7,867,969 B2
(45) Date of Patent: Jan. 11, 2011

(54) COMPOSITION FOR WASHING KERATIN MATERIALS COMPRISING A MAGNESIUM SALT ANIONIC SURFACTANT

(75) Inventors: Sandrine Decoster, Saint-Gratien (FR); Béatrice Thomas, Issy les Moulineaux (FR)

(73) Assignee: L'Oreal S.A., Paris (FR)

( * ) Notice: Subject to any disclaimer, the term of this patent is extended or adjusted under 35 U.S.C. 154(b) by 76 days.

(21) Appl. No.: 11/589,213

(22) Filed: Oct. 30, 2006

(65) Prior Publication Data

US 2007/0105734 A1 May 10, 2007

Related U.S. Application Data

(60) Provisional application No. 60/736,299, filed on Nov. 15, 2005.

(30) Foreign Application Priority Data

Oct. 28, 2005 (FR) .................... 05 11096

(51) Int. Cl.
*C11D 1/83* (2006.01)
*C11D 3/30* (2006.01)
*C11D 3/37* (2006.01)

(52) U.S. Cl. ............. 510/428; 510/119; 510/123; 510/124; 510/127; 510/130; 510/155; 510/156; 510/332; 510/351; 510/352; 510/490; 510/495; 510/498; 510/499

(58) Field of Classification Search ........... 510/119, 510/123, 127, 130, 124, 155, 156, 332, 351, 510/352, 426, 427, 428, 490, 495, 498, 499
See application file for complete search history.

(56) References Cited

U.S. PATENT DOCUMENTS

| | | | |
|---|---|---|---|
| 2,261,002 A | 10/1941 | Ritter |
| 2,271,378 A | 1/1942 | Searle |
| 2,273,780 A | 2/1942 | Dittmer |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,836,537 A | 9/1974 | Boerwindle et al. |
| 3,874,870 A | 4/1975 | Green et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,165,367 A | 8/1979 | Chakrabarti |
| 4,172,887 A | 10/1979 | Vanlerberghe et al. |
| 4,189,468 A | 2/1980 | Vanlerberghe et al. |
| 4,217,914 A | 8/1980 | Jacquet et al. |
| 4,220,548 A | 9/1980 | Hashimoto et al. |
| 4,223,009 A | 9/1980 | Chakrabarti |
| 4,240,450 A | 12/1980 | Grollier et al. |
| 4,277,581 A | 7/1981 | Vanlerberghe et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,591,610 A | 5/1986 | Grollier |
| 4,608,250 A | 8/1986 | Jacquet et al. |
| 4,761,273 A | 8/1988 | Grollier et al. |
| 4,839,166 A | 6/1989 | Grollier et al. |

(Continued)

FOREIGN PATENT DOCUMENTS

| | | |
|---|---|---|
| CA | 1077849 | 5/1980 |
| EP | 0 080 976 A1 | 6/1983 |
| EP | 0 122 324 A1 | 10/1984 |

(Continued)

OTHER PUBLICATIONS

French Search Report for FR 0511096, dated Jun. 30, 2006.
C.U. Patel, "Anti-static properties of some cationic polymers used in hair care products," International Journal of Cosmetic Science, vol. 5, pp. 181-188 (1983).
M.R. Porter, BSc, PhD, CChem, MRSC, "Handbook of Surfactants," Blackie & Son, Ltd., Glasgow & London, pp. 116-178 (1991).

(Continued)

*Primary Examiner*—Charles I Boyer
(74) *Attorney, Agent, or Firm*—Finnegan, Henderson, Farabow, Garrett & Dunner, LLP

(57) ABSTRACT

Disclosed herein is a composition for washing keratin materials, comprising, in an aqueous medium:
(a) at least one first anionic surfactant in the form of a magnesium salt,
(b) at least one second anionic surfactant different from the first,
(c) at least one amphoteric or zwitterionic surfactant,
(d) at least one oxyethylenated sorbitan ester, and
(e) at least one polymer chosen from cationic polymers and amphoteric or zwitterionic polymers. Also disclosed herein is a cosmetic treatment process comprising applying such a composition to the hair.

32 Claims, No Drawings

U.S. PATENT DOCUMENTS

| | | | |
|---|---|---|---|
| 4,948,576 A * | 8/1990 | Verdicchio et al. | 424/59 |
| 4,948,579 A | 8/1990 | Jacquet et al. | |
| 4,957,732 A | 9/1990 | Grollier et al. | |
| 4,996,059 A | 2/1991 | Grollier et al. | |
| 5,089,252 A | 2/1992 | Grollier et al. | |
| 5,139,037 A | 8/1992 | Grollier et al. | |
| 5,196,189 A | 3/1993 | Jacquet et al. | |
| 5,270,035 A | 12/1993 | Chimento | |
| 6,472,363 B1 * | 10/2002 | Arvanitidou et al. | 510/463 |
| 6,475,499 B2 * | 11/2002 | Maubru et al. | 424/401 |
| 6,525,014 B1 * | 2/2003 | Gorlin et al. | 510/439 |
| 2001/0009909 A1 | 7/2001 | Maubru et al. | |
| 2003/0022799 A1 * | 1/2003 | Alvarado et al. | 510/119 |
| 2004/0105836 A1 * | 6/2004 | Seipel et al. | 424/70.17 |

FOREIGN PATENT DOCUMENTS

| | | |
|---|---|---|
| EP | 0 155 737 A2 | 9/1985 |
| EP | 0 186 507 A2 | 7/1986 |
| EP | 0 337 354 A1 | 10/1989 |
| EP | 0 342 834 A2 | 11/1989 |
| EP | 0 453 238 A1 | 10/1991 |
| EP | 1 043 010 A2 | 10/2000 |
| FR | 1 400 366 | 12/1965 |
| FR | 1 492 597 | 8/1967 |
| FR | 1 583 363 | 9/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 387 031 | 11/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 A1 | 9/1984 |
| FR | 2 584 976 A1 | 5/1987 |
| FR | 2 598 611 A1 | 11/1987 |
| FR | 2 804 020 A1 | 7/2001 |
| GB | 1 021 400 | 3/1966 |
| GB | 1 331 819 | 9/1973 |
| GB | 1 347 051 | 2/1974 |
| GB | 1 479 786 | 7/1977 |
| GB | 1 546 809 | 5/1979 |
| WO | WO 97/26860 | 7/1997 |
| WO | WO 01/39735 A1 | 7/2001 |
| WO | WO 02/05758 A2 | 1/2002 |
| WO | WO 03/057185 A1 | 7/2003 |

OTHER PUBLICATIONS

Charles Todd et al., "Volatile silicone fluids for cosmetic formulations," Cosmetics and Toiletries, vol. 91, pp. 29-32 (1976).
English language abstract of EP 0 080 976 A1, Jun. 8, 1983.
English language abstract of FR 2 584 976 A1 May 7, 1987.

* cited by examiner

COMPOSITION FOR WASHING KERATIN MATERIALS COMPRISING A MAGNESIUM SALT ANIONIC SURFACTANT

This application claims benefit of U.S. Provisional Application No. 60/735,299, filed Nov. 15, 2005, the contents of which are incorporated herein by reference. This application also claims benefit of priority under 35U.S.C. §119 to French Patent Application No. FR 05 11096, filed Oct. 28, 2005, the contents of which are also incorporated herein by reference.

Disclosed herein is an improved cosmetic composition for washing keratin materials, for example, the hair and/or the skin, comprising an original combination of at least one surfactant and at least one polymer. Also, disclosed herein is a cosmetic composition for washing keratin materials, comprising at least two different anionic surfactants, at least one amphoteric or zwitterionic surfactant, at least one oxyethylenated sorbitan ester, and at least one polymer chosen from cationic polymers and amphoteric or zwitterionic polymers. In addition, a cosmetic treatment process using such a cosmetic composition is disclosed.

Numerous gentle washing compositions have been described in the prior art. For example, French Patent Application No. 2 804 020 describes washing compositions, such as shampoos, comprising at least one detergent surfactant and at least one oxyethylenated ester of a fatty acid and of sorbitan having a number of moles of oxyethylene of less than or equal to 10.

U.S. Pat. No. 5,270,035 describes compositions for treating the hair, comprising, in an aqueous medium, sodium cocoamphodiacetate combined with an emulsifier, a surfactant, and an astringent substance based on plant extracts.

European Patent Application No. 0 155 737 describes weakly irritant shampoo compositions intended for individuals with dermatitis. These compositions comprise:
  a betaine,
  at least two anionic surfactants, including triethanolamine lauryl sulphate, and at least one compound chosen from alkali metal alkyl sulphates, N-acylamino acids, and salts thereof, and polyoxyethylene alkyl ether sulphonates, and
  at least one nonionic surfactant chosen from fatty acid alkanolamides and water-soluble polyoxyethylenated products.

European Patent Application No. 0 453 238 describes gentle shampoo compositions, the foaming capacity of which is improved. These compositions comprise, in an aqueous medium, from 8 to 25% by weight of a mixture of surfactants comprising:
  an anionic surfactant,
  an amphoteric surfactant, with the exception of betaines containing phosphorus, and
  an oxyalkylated or glycosidic nonionic surfactant having an HLB of at least 8.

International Patent Application Publication No. WO 02/05758 describes a self-foaming cleansing composition, the foaming capacity and the ease of application of which are improved. This composition comprises at least one self-foaming agent, combined with a mixture of surfactants comprising at least one anionic surfactant, at least one amphoteric surfactant and, optionally, at least one nonionic surfactant. This composition can also comprise at least one cationic conditioner, for example, cationic cellulose derivatives, cationic guar derivatives, and diallyldimethylammonium chloride derivatives and copolymers.

Canadian Patent No. 1 077 849 describes detergent compositions and shampoos which decrease the risks of ocular irritation and the foaming capacity (foam volume and stability) of which is improved. These compositions comprise a surfactant betaine, an anionic surfactant, and a nonionic surfactant comprising a water-soluble polyoxyethylenated derivative and a hydrophobic base, wherein the molar ratio of the amount of betaine to the amount of anionic surfactant ranges from 0.9/1 to 1.1/1.

Finally, International Patent Application Publication No. WO 03/057185 describes cosmetic or dermatological compositions for caring for or cleansing the skin and the hair, which make it possible to combine gentleness with a good cleansing capacity. These compositions are based on a synergistic combination of anionic and nonionic surfactants comprising alkylpolyglycosides, alkyl (ether) sulphates, polyethylene glycol sorbitan esters, and alkyl citrate sulphosuccinates.

However, the compositions described in the prior art have certain insufficiencies, for example, the most effective shampoos can cause stinging in the eyes when the diluted product runs into the eye, which frequently occurs in children. Moreover, a large number of these shampoos cause, in individuals with sensitive skin, discomforting reactions such as redness, itching, and/or stinging.

The gentle compositions proposed in the prior art may also exhibit qualities of use which are unsatisfactory in terms of viscosity and foam quality, and cosmetic properties which are insufficient, for example, in terms of softness and, as regards the hair, of disentangling, smoothing, styling, and/or volume.

The present inventors have now discovered that a combination of surfactants, combined with at least one polymer chosen from cationic polymers and amphoteric or zwitterionic polymers, makes it possible to formulate cosmetic compositions which may be gentle but nevertheless have excellent cosmetic properties. For instance, the presence of an anionic surfactant in the form of a magnesium salt in such compositions may make it possible to obtain compositions which have improved cosmetic properties compared with compositions of the prior art which do not contain such salts.

It has been noted that the compositions according to the present disclosure may provide a better visual smoothness and that the treated hair may be more flexible and may have a better feel. For instance, the compositions of the present disclosure may make it possible to improve disentangling and to increase the lightness and the smoothness of wet hair, and, on dry hair, they may provide greater sheen, and increase the flexibility and smoothness of the hair visually and to the touch.

Thus, the compositions according to the present disclosure may make it possible to decrease the discomforting reactions with the skin and the scalp and may exhibit excellent ocular tolerance. In parallel, they may have good qualities of use and better cosmetic properties, for instance, in terms of softness and, as regards the hair, in addition to softness, in terms of disentangling, smoothing, sheen, flexibility, styling, and/or volume.

Thus disclosed herein is a cosmetic composition for washing keratin materials, comprising, in an aqueous medium:
  (a) at least a first anionic surfactant in the form of a magnesium salt,
  (b) at least a second anionic surfactant different from the first,
  (c) at least one amphoteric or zwitterionic surfactant,
  (d) at least one oxyethylenated sorbitan ester, and
  (e) at least one polymer chosen from cationic polymers and amphoteric or zwitterionic polymers.

Also disclosed herein is a cosmetic treatment process using the composition.

Other subjects and characteristics, aspects, and advantages of the present disclosure will emerge more clearly upon reading the description and the examples which follow.

Anionic Surfactants

According to the present disclosure, the cosmetic composition comprises at least a first anionic surfactant in the form of a magnesium salt. The at least one first anionic surfactant may be chosen, for example, from the magnesium salts of the following compounds: alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, α-olefin sulphonates, paraffin sulphonates, alkylsulphosuccinates, alkyl ether sulphosuccinates, alkylamide sulphosuccinates, alkyl sulphoacetates, acylsarcosinates, acylglutamates, and mixtures thereof, wherein the alkyl and acyl groups of these compounds comprises from 6 to 24 carbon atoms and the aryl group is chosen, for example, from phenyl and benzyl groups.

In at least one embodiment, the at least one first anionic surfactant comprises at least one magnesium alkyl ether sulphate comprising from 1 to 16 ethylene oxide units. According to this embodiment, the alkyl group may be chosen from $C_{8-30}$, for example, $C_{12-24}$alkyl groups.

Non-limiting examples of such a anionic surfactant include magnesium lauryl ether sulphates comprising from 1 to 16 ethylene oxide units, for instance, from 1 to 5 ethylene oxide units.

The at least one first anionic surfactant may be present in the composition according to the present disclosure in an amount of at least 0.1% by weight relative to the total weight of the composition, for example, from 0.1 to 10% by weight, from 0.2 to 8% by weight, or from 0.3 to 2% by weight, relative to the total weight of the composition.

The composition which is the subject of the present disclosure also comprises at least one second anionic surfactant, different from the at least one first anionic surfactant. The at least one second anionic surfactant is thus not in the form of a magnesium salt.

The at least one second anionic surfactant may be chosen, for example, from salts, including salts of alkali metals and alkaline earth metals other than magnesium, such as sodium salts, ammonium salts, amine salts, and aminoalcohol salts of the following compounds: alkyl sulphates, alkyl ether sulphates, alkylamido ether sulphates, alkylaryl polyether sulphates, monoglyceride sulphates, alkyl sulphonates, alkylamide sulphonates, alkylaryl sulphonates, α-olefin sulphonates, paraffin sulphonates, alkylsulphosuccinates, alkyl ether sulphosuccinates, alkylamide sulphosuccinates, alkyl sulphoacetates, acylsarcosinates, and acylglutamates, wherein the alkyl and acyl groups of these compounds comprise from 6 to 24 carbon atoms and the aryl group is chosen from phenyl and benzyl groups.

The at least one second anionic surfactant may also be chosen, for example, from $C_{6-24}$ alkyl monoesters of polyglycoside dicarboxylic acids, such as alkyl glucoside citrates, alkyl polyglycoside tartrates, and alkyl polyglycoside sulphosuccinates, alkyl sulphosuccinamates, acylisethionates, and N-acyl taurates, wherein the alkyl or acyl group of these compounds comprises, for example, from 12 to 20 carbon atoms.

According to another embodiment, the at least one second anionic surfactant may be chosen from acyl lactylates, wherein the acyl group comprises from 8 to 20 carbon atoms.

Further examples include, but are not limited to, alkyl-D-galactosid-uronic acids and salts thereof, polyoxyalkylenated ($C_{6-24}$ alkyl) ether carboxylic acids, polyoxyalkylenated ($C_{6-24}$ alkyl)($C_{6-24}$ aryl) ether carboxylic acids, polyoxyalkylenated ($C_{6-24}$ alkyl) amido ether carboxylic acids, and salts thereof, for instance, those comprising from 2 to 50 ethylene oxide units, and mixtures thereof.

In one embodiment, the at least one second anionic surfactant may be chosen from alkyl sulphates, alkyl ether sulphates, and mixtures thereof. Such surfactants may be in the form of alkali metal salts (such sodium salts) and alkaline earth metal salts, ammonium salts, amine salts, and aminoalcohol salts.

The at least one second anionic surfactant may be present in the composition of the present disclosure in an amount of at least 0.5% by weight relative to the total weight of the composition, for example, from 0.5 to 20% by weight, from 1 to 20% by weight, or from 3 to 15% by weight, relative to the total weight of the composition.

Amphoteric or Zwitterionic Surfactants

In addition, the composition according to the present disclosure may comprise at least one amphoteric or zwitterionic surfactant.

The at least one amphoteric or zwitterionic surfactant may be chosen, for instance, from derivatives of secondary or tertiary aliphatic amines in which the aliphatic group is a linear or branched chain comprising from 8 to 22 carbon atoms and comprising at least one anionic group such as carboxylate, sulphonate, sulphate, phosphate, and phosphonate groups; ($C_{8-20}$)alkylbetaines; sulphobetaines; ($C_{8-20}$ alkyl)amido($C_{6-8}$ alkyl)betaines; and ($C_{8-20}$ alkyl)amido($C_{6-8}$ alkyl)sulphobetaines.

Non-limiting examples of amine derivatives include the products sold under the name MIRANOL®, as described, for instance, in U.S. Pat. Nos. 2,528,378 and 2,781,354 and classified in the CTFA dictionary, 3rd Edition, 1982, under the names amphocarboxyglycinate and amphocarboxypropionate having the respective structures (II) and (III):

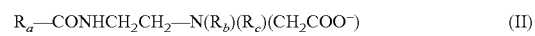

$$R_a\text{—CONHCH}_2\text{CH}_2\text{—N}(R_b)(R_c)(\text{CH}_2\text{COO}^-) \quad (II)$$

wherein:

$R_a$ is chosen from alkyl groups derived from an acid $R_a$—COOH present in hydrolysed coconut oil, hetpyl groups, nonyl groups, and undecyl groups, $R_b$ is a beta-hydroxyethyl group, and $R_c$ is a carboxymethyl group;

and

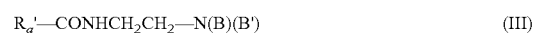

$$R_a'\text{—CONHCH}_2\text{CH}_2\text{—N(B)(B')} \quad (III)$$

wherein:

B is —CH$_2$CH$_2$OX',

B' is —(CH$_2$)$_z$—Y', wherein z=1 or 2,

X' is chosen from —CH$_2$CH$_2$—COOH and hydrogen,

Y' is chosen from —COOH and —CH$_2$—CHOH—SO$_3$H, and $R_a'$ is chosen from alkyl groups of an acid $R_a'$—COOH present in coconut oil and in hydrolysed linseed oil, alkyl groups, for instance, $C_{17}$ alkyl groups and their iso forms, and unsaturated $C_{17}$ groups.

These compounds are classified in the CTFA dictionary, 5th Edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylampho-dipropionate, disodium caprylamphodipropionate, lauroamphodipropionic acid, and cocoamphodipropionic acid.

A non-limiting example of a commercially available product is the cocoamphodiacetate sold by the company RHODIA under the trade name MIRANOL® C2M concentrate.

According to one embodiment, the at least one amphoteric or zwitterionic surfactant may be chosen from $(C_{8-20}$ alkyl) betaines, $(C_{8-20}$ alkyl)amido$(C_{6-8}$ alkyl)betaines, and mixtures thereof.

The at least one amphoteric or zwitterionic surfactant may be present in the composition in an amount of at least 0.1% by weight relative to the total weight of the composition, for instance, from 0.1 to 10% by weight, from 0.5 to 8% by weight, or from 1 to 8% by weight, relative to the total weight of the composition.

Oxyethylenated Sorbitan Esters

The composition according to the present disclosure comprises at least one oxyethylenated sorbitan ester.

The compounds may be chosen, for instance, from oxyethylenated derivatives of monoesters and polyesters of $C_{8-30}$ fatty acids and of sorbitan, comprising from 1 to 50 ethylene oxide units. According to one embodiment, these compounds may be chosen from oxyethylenated derivatives of monoesters and polyesters of $C_{12-24}$ fatty acids and of sorbitan, comprising from 4 to 20 ethylene oxide units.

Such compounds are also known as polysorbates and are sold, for example, under the name TWEEN by the company UNIQEMA. Non-limiting examples of such products include oxyethylene sorbitan monolaurate comprising 4 OE, sold under the name TWEEN 21, oxyethylene sorbitan monolaurate comprising 20 OE, sold under the name TWEEN 20, oxyethylene sorbitan monopalmitate comprising 20 OE, sold under the name TWEEN 40, oxyethylene sorbitan monostearate comprising 20 OE, sold under the name TWEEN 60, oxyethylene sorbitan monostearate comprising 4 OE, sold under the name TWEEN 61, oxyethylene sorbitan tristearate comprising 20 OE, sold under the name TWEEN 65, oxyethylene sorbitan monooleate comprising 20 OE, sold under the name TWEEN 80, oxyethylene sorbitan monooleate comprising 5 OE, sold under the name TWEEN 81, and oxyethylene sorbitan trioleate comprising 20 OE, sold under the name TWEEN 85.

As used herein, and as generally understood in the art, the term "compound comprising X OE" denotes an oxyethylenated compound comprising X oxyethylene units per molecule.

In at least one embodiment, the fatty acid of the oxyethylenated sorbitan ester is a saturated fatty acid.

According to another embodiment, the at least one sorbitan ester is oxyethylene sorbitan monolaurate comprising 4 OE, oxyethylene sorbitan monolaurate comprising 20 OE, and mixtures thereof.

According to a further embodiment, the composition according to the present disclosure comprises a mixture of oxyethylene sorbitan monolaurate comprising 4 OE and oxyethylene sorbitan monolaurate comprising 20 OE.

The at least one oxyethylenated sorbitan ester may be present in the composition in an amount of at least 0.5% by weight relative to the total weight of the composition, for example, from 0.5 to 10% by weight, from 2 to 9% by weight, or from 4 to 8% by weight, relative to the total weight of the composition.

Polymers

The composition according to the present disclosure may also comprise at least one polymer chosen from cationic polymers and amphoteric or zwitterionic polymers.

Cationic Polymers

As used herein, the term "cationic polymer" is intended to mean any polymer containing at least one cationic group and/or at least one group which can be ionized to a cationic group.

The cationic polymers which can be used in accordance with the present disclosure may be chosen from all those known in the art to improve the cosmetic properties of hair treated with detergent compositions, for example, those described in European Patent Application No. 0 337 354 and French Patent Application Nos. 2 270 846, 2 383 660, 2 598 611, 2 470 596, and 2 519 863.

In one embodiment, the cationic polymers are chosen, for example, from those which comprise units comprising at least one group chosen from primary, secondary, tertiary, and quaternary amine groups which can either be part of the main polymer chain, or can be carried by a side substituent directly connected to the chain.

The cationic polymers may have a weight-average molecular mass of greater than $10^5$, for example, greater than $10^6$, or ranging from $10^6$ to $10^8$.

According to another embodiment, the cationic polymers may be chosen, for instance, from polyamine, polyaminoamide, and polyquaternary ammonium polymers, such as those described in French Patent Nos 2 505 348 and 2 542 997. Non-limiting examples of these polymers include:

(1) homopolymers and copolymers derived from acrylic or methacrylic esters and amides and comprising at least one unit chosen from units of the following formulas:

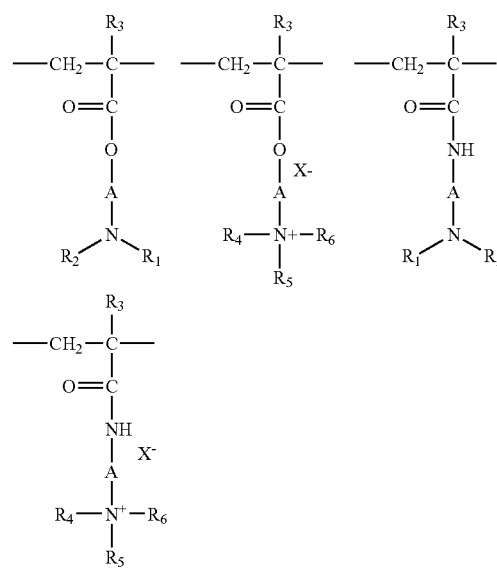

wherein:

$R_1$ and $R_2$, which may be identical or different, are chosen from hydrogen and alkyl groups comprising from 1 to 6 carbon atoms, for instance, methyl and ethyl groups;

$R_3$, which may be identical or different, is chosen from hydrogen and $CH_3$;

the symbols A, which may be identical or different, are chosen from linear or branched alkyl groups comprising from 1 to 6 carbon atoms, for example, from 2 to 3 carbon atoms and hydroxyalkyl groups comprising from 1 to 4 carbon atoms;

$R_4$, $R_5$, and $R_6$, which may be identical or different, are chosen from alkyl groups comprising from 1 to 18 carbon atoms and benzyl groups, and in at least one embodiment, alkyl groups comprising from 1 to 6 carbon atoms; and X is an anion derived from an inorganic or organic acid, such as methosulphate anions and halides, for instance chloride and bromide.

The copolymers of family (1) may also comprise at least one unit derived from comonomers which may be chosen from acrylamides, methacrylamides, diacetone acrylamides, acrylamides and methacrylamides substituted on the nitrogen atom with ($C_1$-$C_4$) lower alkyl groups, groups derived from acrylic or methacrylic acids and esters thereof, vinyllactams such as vinylpyrrolidone and vinylcaprolactam, and vinyl esters.

Examples of copolymers of family (1) include, but are not limited to:

- copolymers of acrylamide and of dimethylaminoethyl methacrylate quaternized with dimethyl sulphate or with a dimethyl halide,
- copolymers of acrylamide and of methacryloyloxyethyltrimethylammonium chloride described, for example, in European Patent Application No. 0 080 976,
- copolymers of acrylamide and of methacryloyloxyethyltrimethylammonium methosulphate,
- quaternized or nonquaternized vinylpyrrolidone/dialkylaminoalkyl acrylate or methacrylate copolymers, described, for example, in French Patent Nos. 2 077 143 and 2 393 573,
- dimethylaminoethyl methacrylate/vinylcaprolactam/vinylpyrrolidone terpolymers,
- vinylpyrrolidone/methacrylamidopropyldimethylamine copolymers, and
- quaternized vinylpyrrolidone/dimethylaminopropylmethacrylamide copolymers.

(2) Cellulose ether derivatives comprising quaternary ammonium groups described, for example, in French Patent No. 1 492 597, such as the polymers sold under the names "JR" (JR 400, JR 125, JR 30M) or "LR" (LR 400, LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers and cellulose derivatives grafted with a water-soluble monomer of quaternary ammonium, and described, for example, in U.S. Pat. No. 4,131,576, such as hydroxyalkylcelluloses, for instance, hydroxymethyl-, hydroxyethyl-, and hydroxypropylcelluloses grafted, for example, with a salt chosen from methacryloylethyltrimethylammonium, methacrylamidopropyltrimethylammonium, and dimethyldiallylammonium salts.

Commercial products corresponding to these polymers include, for example, the products sold under the name "Celquat® L 200" and "Celquat® H 100" by the company National Starch.

(4) Non-cellulose-based cationic polysaccharides described in U.S. Pat. Nos. 3,589,578 and 4,031,307, such as guar gums comprising cationic trialkylammonium groups. Guar gums modified with a salt, for example the chloride, of 2,3-epoxypropyltrimethylammonium may also be used.

Such products are sold, for instance, under the trade names JAGUAR® C13 S, JAGUAR® C15, JAGUAR® C17, and JAGUAR® C162 by the company MEYHALL.

(5) Polymers comprising piperazinyl units and divalent alkylene or hydroxyalkylene groups comprising straight or branched chains, optionally interrupted with at least one entity chosen from oxygen, sulphur, nitrogen, aromatic rings, and heterocyclic rings, and also the oxidation and/or quaternization products of these polymers. Such polymers are described, for example, in French Patent Nos. 2 162 025 and 2 280 361.

(6) Water-soluble polyamino amides prepared, for example, by polycondensation of an acidic compound with a polyamine; these polyamino amides possibly being crosslinked with an entity chosen from epihalohydrins; diepoxides; dianhydrides; unsaturated dianhydrides; bisunsaturated derivatives; bishalohydrins; bisazetidiniums; bishaloacyidiamines; bisalkyl halides; oligomers resulting from the reaction of a difunctional compound which is reactive with an entity chosen from bishalohydrins, bisazetidiniums, bishaloacyldiamines, bisalkyl halides, epihalohydrins, diepoxides, and bisunsaturated derivatives; the crosslinking agent being used in an amount ranging from 0.025 to 0.35 mol per amine group of the polyamino amide; these polyamino amides optionally being alkylated or, if they comprise at least one tertiary amine function, they may be quaternized. Such polymers are described, for example, in French Patent Nos. 2 252 840 and 2 368 508.

(7) Polyamino amide derivatives resulting from the condensation of polyalkylene polyamines with polycarboxylic acids, followed by alkylation with difunctional agents, for example, adipic acid/dialkylaminohydroxyalkyldialkylenetriamine polymers in which the alkyl group comprises from 1 to 4 carbon atoms, such as methyl, ethyl, and propyl groups, and the alkylene group comprises from 1 to 4 carbon atoms, such as an ethylene group. Such polymers are described, for instance, in French Patent No. 1 583 363. In at least one embodiment, these derivatives may be chosen from adipic acid/dimethylaminohydroxypropyldiethylenetriamine polymers.

(8) Polymers obtained by reaction of a polyalkylene polyamine comprising two primary amine groups and at least one secondary amine group, with a dicarboxylic acid chosen from diglycolic acid and saturated aliphatic dicarboxylic acids comprising from 3 to 8 carbon atoms. The molar ratio of the polyalkylene polyamine to the dicarboxylic acid may range from 0.8:1 to 1.4:1; the polyamino amide resulting therefrom being reacted with epichlorohydrin in a molar ratio of epichlorohydrin relative to the secondary amine group of the polyamino amide ranging from 0.5:1 to 1.8:1. Such polymers are described, for example, in U.S. Pat. Nos. 3,227,615 and 2,961,347.

(9) Cyclopolymers of alkyldiallylamine and cyclopolymers of dialkyldiallyl-ammonium, such as homopolymers and copolymers comprising, as main constituent of the chain, at least one unit chosen from units of formulas (Va) and (Vb):

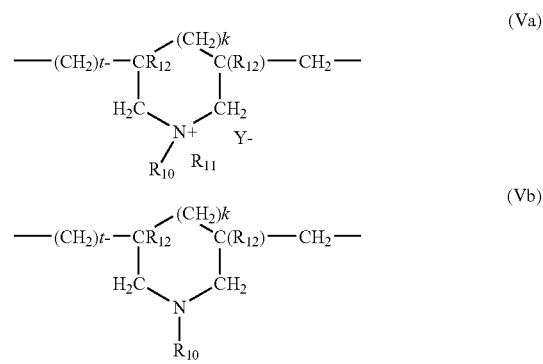

wherein:
k and t, which may be identical or different, are equal to 0 or 1, the sum k+t being equal to 1;
$R_{12}$ is chosen from hydrogen and methyl groups;
$R_{10}$ and $R_{11}$, which may be identical or different, are chosen from alkyl groups comprising from 1 to 6 carbon atoms, hydroxyalkyl groups in which the alkyl group comprises, for example, from 1 to 5 carbon atoms, and lower ($C_1$-$C_4$)amidoalkyl groups, or $R_{10}$ and $R_{11}$ may form, together with the nitrogen atom to which they are attached, heterocyclic groups such as piperidinyl and morpholinyl; and Y' is an anion such as bromide, chloride, acetate, borate, citrate, tartrate, bisulphate, bisulphite, sulphate, and phosphate. These polymers are described, for example, in French Patent No. 2 080 759 and in its Certificate of Addition 2 190 406.

In one embodiment, $R_{10}$ and $R_{11}$, which may be identical or different, are chosen from alkyl groups comprising from 1 to 4 carbon atoms.

Examples of such polymers include, but are not limited to, the dimethyldiallylammonium chloride homopolymer sold under the name "MERQUAT® 100" by the company CAL-GON (and its homologues of low weight-average molecular mass) and the copolymers of diallyldimethylammonium chloride and of acrylamide sold under the name "MER-QUAT® 550".

(10) Quaternary diammonium polymers comprising at least one repeating unit of formula (VI):

wherein:
$R_{13}$, $R_{14}$, $R_{15}$, and $R_{16}$, which may be identical or different, are chosen from aliphatic, alicyclic, and arylaliphatic groups comprising from 1 to 20 carbon atoms and lower hydroxyalkyl aliphatic groups, or alternatively $R_{13}$, $R_{14}$, $R_{15}$, and $R_{16}$ may form, together or separately, with the nitrogen atoms to which they are attached, heterocycles optionally comprising a second heteroatom other than nitrogen, or alternatively $R_{13}$, $R_{14}$, $R_{15}$, and $R_{16}$, which may be identical or different, are chosen from linear or branched $C_1$-$C_6$ alkyl groups substituted with at least one group chosen from nitrile groups, ester groups, acyl groups, amide groups, —CO—O—$R_{17}$-E groups, and —CO—NH—$R_{17}$-E groups, wherein $R_{17}$ is an alkylene group and E is a quaternary ammonium group;

$A_1$ and $B_1$, which may be identical or different, are chosen from polymethylene groups comprising from 2 to 20 carbon atoms, which may be linear or branched, saturated or unsaturated, and which may comprise, linked or intercalated in the main chain, at least one entity chosen from aromatic rings, oxygen, sulphur, sulphoxide groups, sulphone groups, disulphide groups, amino groups, alkylamino groups, hydroxyl groups, quaternary ammonium groups, ureido groups, amide groups, and ester groups, and $X^-$ is an anion derived from an inorganic or organic acid;
$A_1$, $R_{13}$, and $R_{15}$ may form, together with the two nitrogen atoms to which they are attached, a piperazine ring;
if $A_1$ is chosen from linear or branched, saturated or unsaturated alkylene or hydroxyalkylene groups, $B_1$ may be chosen from:

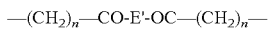

wherein E' is chosen from:
a) glycol residues of formula —O—Z—O—, wherein Z is chosen from linear or branched hydrocarbon-based groups and groups of the following formulas:

—($CH_2$—$CH_2$—O)$_x$—$CH_2$—$CH_2$—

—[$CH_2$—CH($CH_3$)—O]$_y$—$CH_2$—CH($CH_3$)— wherein x and y, which may be identical or different, are chosen from integers ranging from 1 to 4, which represent a defined and unique degree of polymerization, and numbers ranging from 1 to 4, which represent an average degree of polymerization;

b) bis-secondary diamine residue such as piperazine derivatives;

c) bis-primary diamine residues of formula —NH—Y—NH—, wherein Y is chosen from linear or branched hydrocarbon-based groups and the divalent group —$CH_2$—$CH_2$—S—S—$CH_2$—$CH_2$—; and d) ureylene groups of formula —NH—CO—NH—.

In at least one embodiment, $X^-$ is an anion such as chloride or bromide.

Polymers of this type are described, for example, in French Patent Nos. 2 320 330; 2 270 846; 2 316 271; 2 336 434; and 2 413 907 and U.S. Pat. Nos. 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; and 4,027,020.

Non-limiting examples of such polymers include those comprising at least one repeating unit of formula (VII):

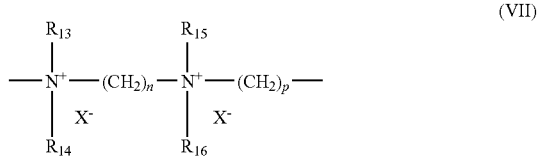

wherein $R_{13}$, $R_{14}$, $R_{15}$, and $R_{16}$, which may be identical or different, are chosen from alkyl and hydroxyalkyl groups comprising from 1 to 4 carbon atoms, n and p, which may be identical or different, are integers ranging from 2 to 20, and $X^-$ is an anion derived from an inorganic or organic acid.

(11) Polyquaternary ammonium polymers comprising units of formula (VIII):

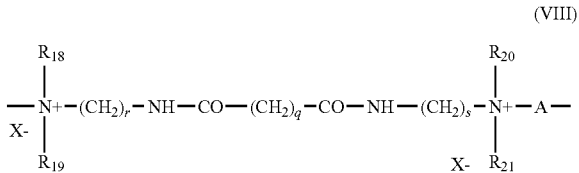

wherein:
$R_{18}$, $R_{19}$, $R_{20}$, and $R_{21}$, which may be identical or different, are chosen from hydrogen, methyl groups, ethyl groups, propyl groups, β-hydroxyethyl groups, β-hydroxypropyl groups, —$CH_2CH_2(OCH_2CH_2)_p$OH groups, wherein p is chosen from integers ranging from 0 to 6, with the proviso that $R_{18}$, $R_{19}$, $R_{20}$, and $R_{21}$ are not simultaneously hydrogen, r and s, which may be identical or different, are chosen from integers ranging from 1 to 6, q is chosen from integers ranging from 0 to 34, X⁻ is an anion such as a halide, and A is chosen from radicals of dihalides and —CH₂—CH₂—O—CH₂—CH₂—.

Such compounds are described, for instance, in European Patent Application No. 0 122 324.

(12) Quaternary polymers of vinylpyrrolidone and of vinylimidazole.

(13) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with a compound containing olefinic unsaturation, for example, methylenebisacrylamide.

Other examples of suitable cationic polymers include, but are not limited to, cationic proteins and cationic protein hydrolysates, polyalkyleneimines, such as polyethyleneimines, polymers comprising units chosen from vinylpyridine and vinylpyridinium units, condensates of polyamines and of epichlorohydrin, quaternary polyureylenes, and chitin derivatives.

According to one embodiment of the present disclosure, the at least one cationic polymer is chosen from cellulose ether derivatives comprising quaternary ammonium groups, such as the products sold under the name "JR 400" by the company UNION CARBIDE CORPORATION, cationic cyclopolymers, for instance, the homo-polymers and copolymers of dimethyldiallylammonium chloride sold under the names MERQUAT® 100, MERQUAT® 550, and MERQUAT® S by the company CALGON, guar gums modified with a 2,3-epoxypropyltrimethylammonium salt, and quaternary polymers of vinylpyrrolidone and of vinylimidazole.

The at least one cationic polymer may be present in the composition of the present disclosure in an amount of at least 0.01% by weight relative to the total weight of the composition, for example, from 0.05 to 10% by weight, from 0.1 to 5% by weight, or from 0.1 to 2% by weight, relative to the total weight of the composition.

Amphoteric or Zwitterionic Polymers

The amphoteric or zwitterionic polymers which may be used in accordance with the present disclosure may be chosen from polymers comprising K and M units distributed randomly in the polymer chain, wherein K is chosen from units derived from monomers comprising at least one basic nitrogen atom and M is chosen from units derived from acidic monomers comprising at least one group chosen from carboxylic and sulphonic groups, or alternatively, K and M are chosen from groups derived from zwitterionic monomers of carboxybetaines and groups derived from zwitterionic monomers of sulphobetaines.

K and M may also be chosen from cationic polymer chains comprising at least one group chosen from primary, secondary, tertiary, and quaternary amine groups, wherein at least one of the amine groups bears a group chosen from carboxylic and sulphonic groups connected via a hydrocarbon-based radical, or alternatively, K and M may be part of a chain of a polymer comprising an α,β-dicarboxylic ethylene unit in which one of the carboxylic groups has been reacted with a polyamine comprising at least one group chosen from primary and secondary amine groups.

Examples of such amphoteric polymers include, but are not limited to, the following polymers:

(1) Polymers resulting from the copolymerization of a monomer derived from a vinyl compound bearing a carboxylic group, such as acrylic acid, methacrylic acid, maleic acid, and alpha-chloroacrylic acid, and of a basic monomer derived from a substituted vinyl compound comprising at least one basic atom, such as dialkylaminoalkyl methacrylate, dialkylaminoalkyl acrylate, dialkylaminoalkylmethacrylamide, and dialkylaminoalkylacrylamide. Such compounds are described, for example, in U.S. Pat. No. 3,836,537. Another non-limiting example includes the sodium acrylate/acrylamidopropyltrimethylammonium chloride copolymer sold under the name POLYQUART KE 3033 by the company COGNIS.

The vinyl compound may also be a dialkyldiallylammonium salt such as the salt (for example, chloride) of dimethyldiallylammonium. Copolymers of acrylic acid and of the latter monomer are sold under the names MERQUAT 280 and MERQUAT 295 by the company NALCO.

(2) Polymers comprising at least unit derived:

a) from at least one monomer chosen from acrylamides and methacrylamides substituted on the nitrogen with an alkyl radical, b) from at least one acidic comonomer comprising at least one reactive carboxylic group, and c) from at least one basic comonomer, such as acrylic and methacrylic acid esters comprising at least one substituent chosen from primary, secondary, tertiary, and quaternary amine substituents and the product of quaternization of dimethylaminoethyl methacrylate with dimethyl sulphate or diethyl sulphate.

The N-substituted acrylamides or methacrylamides which may be used in accordance with the present disclosure include groups in which the alkyl radicals contain from 2 to 12 carbon atoms, for instance, N-ethyl acrylamide, N-tert-butylacrylamide, N-tert-octylacrylamide, N-octylacrylamide, N-decylacrylamide and N-dodecylacrylamide, and also the corresponding methacrylamides.

The acidic comonomers may be chosen, for example, from acrylic acid, methacrylic acid, crotonic acid, itaconic acid, maleic acid, fumaric acid, and alkyl monoesters, comprising from 1 to 4 carbon atoms, of maleic and fumaric acids and anhydrides.

The basic comonomers may include, for instance, aminoethyl methacrylate, butylaminoethyl methacrylate, N,N'-dimethylaminoethyl methacrylate, and N-tert-butylaminoethyl methacrylate.

Copolymers whose CTFA (4th Edition, 1991) name is octylacrylamide/acrylates/butylaminoethyl methacrylate copolymer may also be used.

(3) Partially or completely alkylated and crosslinked polyaminoamides derived from polyaminoamides of formula (IX):

(IX)

wherein $R_4$ is chosen from divalent radicals derived from a saturated dicarboxylic acid, divalent radicals derived from an aliphatic monocarboxylic or dicarboxylic acid with an ethylenic double bond, divalent radicals derived from an ester of a lower alkanol comprising from 1 to 6 carbon atoms, of these acids, and divalent radicals derived from a radical derived from the addition of any one of the acids with a bis-primary or bis-secondary amine, and Z is chosen from radicals of a polyalkylene/bis-primary, mono, or bis-secondary polyamine, for example:

a) in an amount ranging from 60 to 100 mol %, the radical

(X)

wherein x=2 and p=2, or x=3 and p=2 this radical deriving from a compound chosen from diethylenetriamine, triethylenetetraamine, and dipropylenetriamine;

b) in an amount ranging from 0 to 40 mol %, the radical (X) above, in which x=2 and p=1 and which derives from ethylenediamine, or the radical derived from piperazine:

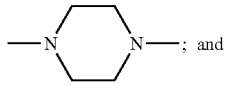; and c) in an amount ranging from 0 to 20 mol %, the radical —NH—$(CH_2)_6$—NH— derived from hexamethylenediamine, these polyaminoamides being crosslinked by addition of a bifunctional crosslinking agent chosen from epihalohydrins, diepoxides, dianhydrides, and bisunsaturated derivatives, by means of 0.025 to 0.35 mol of crosslinking agent per amine group of the polyaminoamide, and alkylated by the action of a compound chosen from acrylic acid, chloroacetic acid, alkane sultone, and salts thereof.

The saturated carboxylic acids may be chosen, for instance, from acids comprising from 6 to 10 carbon atoms, such as adipic acid, 2,2,4-trimethyladipic acid, 2,4,4-trimethyladipic acid, terephthalic acid, and acids with an ethylenic double bond, such as acrylic acid, methacrylic acid, and itaconic acid.

The alkane sultones used in the alkoxylation may be chosen from propane sultone and butane sultone, and the salts of the alkylating agents may be sodium and potassium salts.

(4) Polymers comprising zwitterionic units of formula (XI):

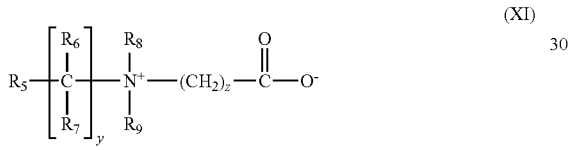

wherein
  $R_5$ is chosen from polymerizable unsaturated groups such as acrylate, methacrylate, acrylamide, and methacrylamide groups,
  y and z, which may be identical or different, are chosen from integers ramging from 1 to 3,
  $R_6$ and $R_7$ are chosen from hydrogen, methyl groups, ethyl groups, and propyl groups, and
  $R_8$ and $R_9$ are chosen from hydrogen and alkyl radicals such that the sum of the number of carbon atoms in $R_8$ and $R_9$ does not exceed 10.

The polymers comprising such units may also comprise units derived from non-zwitterionic monomers, such as dimethyl or diethylaminoethyl acrylates, dimethyl or diethylminoethyl methacrylates, alkyl acrylates, alkyl methacrylates, acrylamides, methacrylamides, and vinyl acetate.

A non-limiting example of such polymers is butyl methacrylate/dimethyl carboxymethylammonioethyl methacrylate copolymer.

(5) Polymers derived from chitosan derivatives comprising monomer units chosen from those of formulas (XII), (XIII), and (XIV):

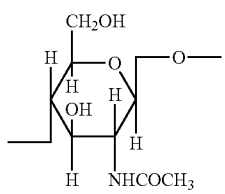

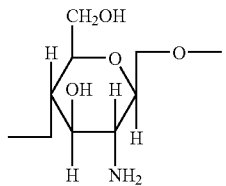

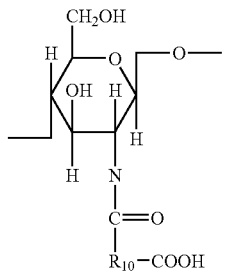

wherein the unit (XII) is present in an amount ranging from 0 to 30%, the unit (XIII) is present in an amount ranging from 5 to 50%, and the unit (XIV) is present in an amount ranging from 30 to 90%, and wherein in this unit (XIV), $R_{10}$ is chosen from radicals of formula:

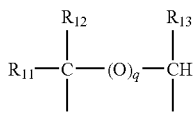

wherein:
  when q=0, $R_{11}$, $R_{12}$, and $R_{13}$, which may identical or different, are chosen from hydrogen, methyl groups, hydroxyl groups, acetoxy groups; amino residues, monoalkoylamine residues, and dialkoylamine residues optionally interrupted with at least one nitrogen atom and/or optionally substituted with at least one group chosen from amine, hydroxyl, carboxyl, alkoylthio and sulphonic groups; and alkoylthio residues in which the alkyl group bears an amino residue, and at least one of the radicals $R_{11}$, $R_{12}$, and $R_{13}$ being, in this case, a hydrogen atom; and
  when q=1, $R_{11}$, $R_{12}$, and $R_{13}$ are hydrogen; and
  the acid and base addition salts thereof.

(6) Polymers derived from the N-carboxyalkylation of chitosan, such as N-carboxymethyl chitosan or N-carboxybutyl chitosan.

(7) Polymers of formula (XV), such as those described, for example, in French Patent No. 1 400 366:

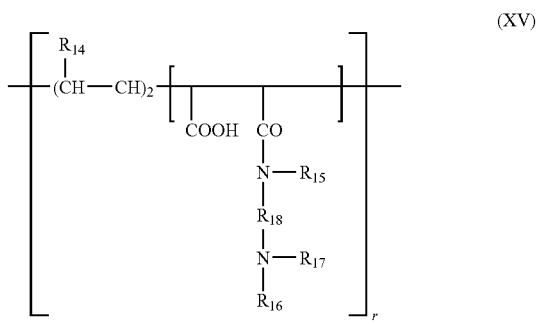

wherein:
r is an integer greater than or equal to 1,
$R_{14}$ is chosen from hydrogen, $CH_3O$ radicals, $CH_3CH_2O$ radicals, and phenyl radicals,
$R_{15}$ is chosen from hydrogen and lower alkyl radicals such as methyl and ethyl,
$R_{16}$ is chosen from hydrogen and lower alkyl radicals such as methyl and ethyl,
$R_{17}$ is chosen from lower alkyl radicals such as methyl or ethyl and radicals of the formula: —$R_{18}$—$N(R_{16})_2$, and
$R_{18}$ is chosen from —$CH_2$—$CH_2$— groups, —$CH_2$—$CH_2$—$CH_2$— groups, and —$CH_2$—$CH(CH_3)$—, wherein $R_{16}$ is defined above, and
the higher homologues of these radicals comprising up to 6 carbon atoms.

(8) Amphoteric polymers of formula -D-X-D-X-, chosen from:

a) polymers obtained by the action of chloroacetic acid or sodium chloroacetate on compounds comprising at least one unit of formula:

-D-X-D-X-D- wherein D is the radical

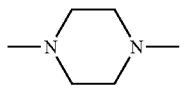

and X is chosen from symbols E and E', wherein E or E', which may be identical or different, are chosen from divalent radicals which may be straight- or branched-chain alkylene radicals comprising up to 7 carbon atoms in the main chain, which may be unsubstituted or substituted with hydroxyl groups and which may also comprise at least one entity chosen from oxygen, nitrogen, sulphur, 1 to 3 aromatic rings, and/or 1 to 3 heterocyclic rings; wherein the oxygen, nitrogen, and sulphur atoms are present in the form of at least one group chosen from ethyl, thioether, sulphoxide, sulphone, sulphonium, alkylamine, alkenylamine, hydroxyl, benzylamine, amine oxide, quaternary ammonium, amide, imide, alcohol, ester, and/or urethane groups;

b) polymers of formula:

-D-X-D-X— wherein D is the radical

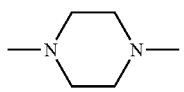

and X is chosen from the symbols E and E' and at least once E'; wherein E has the meaning given above and E' is chosen from divalent radicals which may be straight- or branched-chain alkylene radicals comprising up to 7 carbon atoms in the main chain, which may be unsubstituted or substituted with at least one hydroxyl radical and may comprise at least one nitrogen atom, the nitrogen atom being substituted with an alkyl chain optionally interrupted with an oxygen atom and comprising at least one function chosen from carboxyl functions and hydroxyl functions, betainized by reaction with chloroacetic acid or sodium chloroacetate.

(9) Copolymers of ($C_1$-$C_5$)alkyl vinyl ether/maleic anhydride partially modified by semi-amidation with an N,N-dialkylaminoalkylamine such as N,N-dimethylamino-propylamine or by semiesterification with an N,N-dialkanolamine. These copolymers may also comprise other vinyl comonomers such as vinylcaprolactam.

According to at least one embodiment of the present disclosure, the at least one amphoteric or zwitterionic polymer may be chosen from those of family (1) described above.

The at least one amphoteric or zwifterionic polymer may be present in the composition in an amount of at least 0.01% by weight relative to the total weight of the composition, for example, from 0.05 to 10% by weight, from 0.1 to 5% by weight, or from 0.1 to 2% by weight, relative to the total weight of the composition.

According to one embodiment, the composition according to the present disclosure comprises at least two different polymers, chosen from cationic polymers and amphoteric or zwitterionic polymers.

In another embodiment, the composition comprises at least one cationic polymer and at least one amphoteric or zwitterionic polymer.

The composition according to the present disclosure may also comprise, in addition to the at least one oxyethylenated sorbitan ester, at least one additional nonionic surfactants, different from the former.

Examples of additional nonionic surfactants which may be used in the compositions of the present disclosure are described, for example, in "Handbook of Surfactants" by M. R. PORTER, publisher Blackie & Son (Glasgow and London), 1991, pp 116-178. These nonionic surfactants may be chosen, for instance, from alcohols; alpha-diols; ($C_{1-20}$)alkylphenols; and polyethoxylated, polypropoxylated, and polyglycerolated fatty acids having a fatty chain comprising, for example, from 8 to 18 carbon atoms, it being possible for the number of ethylene oxide or propylene oxide groups to range, for example, from 2 to 50 and for the number of glycerol groups to range, for example, from 2 to 30.

Further examples include, but are not limited to, condensates of ethylene oxide and of propylene oxide with fatty alcohols; polyethoxylated fatty amides comprising, for example, from 2 to 30 ethylene oxide units, polyglycerolated fatty amides comprising, on average, from 1 to 5 glycerol groups, for example, from 1.5 to 4, fatty acid esters of saccharose, fatty acid esters of polyethylene glycol, ($C_{6-24}$alkyl)polyglycosides, N—($C_{6-24}$ alkyl)glucamine derivatives, and amine oxides such as ($C_{10-14}$alkyl)amine oxides and N—($C_{10-14}$ acyl)aminopropylmorpholine oxides.

The at least one additional nonionic surfactant may be present in the composition in an amount ranging from 0.01 to 10% by weight, for example, from 0.05 to 5% by weight relative to the total weight of the composition.

According to at least one embodiment, the composition according to the present disclosure may have a total surfactant content (of anionic, nonionic, and amphoteric or zwitterionic surfactants) ranging from 4 to 50% by weight, for example, from 4 to 20% by weight, relative to the total weight of the composition.

The compositions according to the present disclosure may also comprise at least one cationic surfactant.

Examples of cationic surfactants include, but are not limited to, optionally polyoxyalkylenated primary, secondary, or tertiary fatty amine salts; quaternary ammonium salts such as tetraalkylammonium chlorides and bromides, alkyl-amidoalkyltrialkylammonium chlorides and bromides, trialkylbenzylammonium chlorides and bromides, trialkylhydroxylalkylammonium chlorides and bromides and alkylpyridinium chlorides and bromides; imidazoline derivatives; and amine oxides which are cationic in nature.

The at least one cationic surfactant may be present in the composition in an amount ranging from 0.01 to 10% by weight, for example, from 0.05 to 5% by weight, or from 0.3 to 3% by weight relative to the total weight of the cosmetic composition.

The composition according to the present disclosure may also comprise at least one silicone.

The silicones which may be used in accordance with the present disclosure may be soluble or insoluble in the composition, for example, polyorganosiloxanes which are insoluble in the composition, and may be in a form chosen from oils, waxes, resins, and gums.

The insoluble silicones may be dispersed in the compositions in the form of particles generally having a number-average size ranging from 2 nanometers to 100micrometers, for example, from 20 nanometers to 20 micrometers (as measured with a particle sizer).

Suitable polyorganosiloxanes are defined in greater detail, for example, in the work by Walter NOLL "Chemistry and Technology of Silicones" (1968) Academic Press. They may be volatile or non-volatile.

When they are volatile, the silicones may be chosen, for instance, from those having a boiling point ranging from 60° C. to 260° C., such as:

(i) cyclic silicones comprising from 3 to 7 silicon atoms, for instance, from 4 to 5 silicon atoms, for example, the octamethylcyclotetrasiloxane sold under the name "VOLATILE SILICONE 7207" by UNION CARBIDE and "SILBIONE 70045 V 2" by RHODIA, the decamethylcyclopentasiloxane sold under the name "VOLATILE SILICONE 7158" by UNION CARBIDE and "SILBIONE 70045 V 5" by RHODIA, and mixtures thereof.

The at least one silicon may also be chosen from cyclocopolymers of the dimethylsiloxane/methylalkylsiloxane type, such as the "SILICONE VOLATILE FZ 3109" sold by the company UNION CARBIDE, which has the chemical structure:

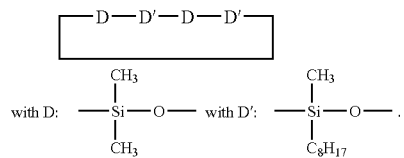

Further examples include mixtures of cyclic silicones with silicon-derived organic compounds, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy)bisneopentane;

(ii) linear volatile silicones comprising from 2 to 9 silicon atoms and having a viscosity of less than or equal to $5 \times 10^{-6}$ m$^2$/s at 25° C. These compounds include, for example, the decamethyltetrasiloxane sold under the name "SH 200" by the company TORAY SILICONE. Silicones which fall into this class are also described in the article published in Cosmetics and toiletries, Vol. 91, January 76, p. 27-32— TODD & BYERS "Volatile Silicone fluids for cosmetics".

Examples of suitable non-volatile silicones include, but are not limited to, polyalkylsiloxanes, polyarylsiloxanes, polyalkylarylsiloxanes, silicone gums and resins, polyorganosiloxanes modified with organofunctional groups, polysiloxane(A)-polyoxyalkylene(B) linear block copolymers of (A-B)$_n$ type wherein n>3; grafted silicone polymers, with a non-silicone organic backbone, comprising an organic main chain formed from organic monomers containing no silicone, onto which is grafted, within the chain and also, optionally, on at least one of its ends, at least one polysiloxane macromonomer; grafted silicone polymers, with a polysiloxane backbone grafted with non-silicone organic monomers, comprising a main chain of polysiloxane onto which is grafted, within the chain and also, optionally, on at least one of its ends, at least one organic macromonomer containing no silicone; and mixtures thereof.

Non-limiting examples of polyalkylsiloxanes include polydimethylsiloxanes with trimethylsilyl end groups having a viscosity ranging from $5 \times 10^{-6}$ to 2.5 m$^2$/s at 25° C., for example, from $1 \times 10^{-5}$ to 1 m$^2$/s. The viscosity of the silicones is, for example, measured at 25° C. according to ASTM standard 445 Appendix C.

These polyalkylsiloxanes include, for instance, the following commercial products:

the SILBIONE oils of the 47 and 70 047 series and the MIRASIL oils sold by RHONE POULENC, such as the 70 047 V 500 000 oil;

the oils of the MIRASIL series sold by the company RHONE POULENC;

the oils of the 200 series from the company DOW CORNING, such as DC200 having a viscosity of 60 000 cSt; and the VISCASIL oils from GENERAL ELECTRIC and some oils of the SF series (SF 96, SF 18) from GENERAL ELECTRIC.

Other examples include, but are not limited to, polydimethylsiloxanes with dimethylsilanol end groups (dimethiconol according to the CTFA name), such as the oils of the 48 series from the company RHONE POULENC.

Further examples include, but are not limited to, the products sold under the names "ABIL WAX 9800 and 9801" by the company GOLDSCHMIDT, which are poly(C$_1$-C$_{20}$) alkylsiloxanes.

The polyalkylarylsiloxanes may be chosen, for instance, from linear and/or branched polydimethylmethylphenylsiloxanes and polydimethyldiphenylsiloxanes having a viscosity ranging from $1 \times 10^{-5}$ to $5 \times 10^{-2}$ m$^2$/s at 25° C.

Examples of these polyalkylarylsiloxanes include, but are not limited to, the products sold under the following names:

the SILBIONE oils of the 70 641 series from RHONE POULENC;

the oils of RHODORSIL 70 633 and 76 series from RHONE POULENC;

the DOW CORNING 556 COSMETIC GRAD FLUID oil from DOW CORNING;

the silicones of the PK series from BAYER, such as the product PK20;

the silicones of the PN and PH series from BAYER, such as the products PN1000 and PH1000; and some oils of the SF series from GENERAL ELECTRIC, such as SF 1023, SF 1154, SF 1250, and SF 1265.

The silicone gums which may be used in accordance with the present disclosure include, for example, polydiorganosiloxanes having high number-average molecular masses ranging from 200 000 to 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, and mixtures thereof.

Non-limiting examples of such silicone gums include the following products:

polydimethylsiloxane, polydimethylsiloxane/methylvinylsiloxane gums, polydimethylsiloxane/diphenylsiloxane, polydimethylsiloxane/phenylmethylsiloxane, and polydimethylsiloxane/diphenylsiloxane/methylvinylsiloxane.

Silicone mixtures may also be used, such as:

the mixtures formed from a polydimethylsiloxane hydroxylated at the end of the chain (called dimethiconol according to the nomenclature of the CTFA dictionary) and a cyclic polydimethylsiloxane (called cyclomethicone according to the nomenclature of the CTFA dictionary), such as the product Q2 1401 sold by the company DOW CORNING;

the mixtures formed from a polydimethylsiloxane gum with a cyclic silicone, such as the product SF 1214 Silicone Fluid from the company GENERAL ELECTRIC; this product is an SF 30 gum corresponding to a dimethicone, having a number-average molecular weight of 500 000 solubilized in the SF 1202 Silicone Fluid oil corresponding to decamethylcyclopentasiloxane; and the mixtures of two PDMSs having different viscosities, for example, a mixture of a PDMS gum and of a PDMS oil, such as the product SF 1236 from the company GENERAL ELECTRIC. The product SF 1236 is the mixture of an SE 30 gum defined above having a viscosity of 20 m$^2$/s and of an SF 96 oil having a viscosity of $5 \times 10^{-6}$ m$^2$/s. This product may comprise 15% of SE 20 gum and 85% of an SF 96 oil.

The organopolysiloxane resins which may be used in accordance with the present disclosure may include crosslinked siloxane systems comprising units chosen from $R_2SiO_{2/2}$, $R_3SiO_{1/2}$, $RSiO_{3/2}$, and $SiO_{4/2}$, wherein R is chosen from hydrocarbon-based groups comprising from 1 to 16 carbon atoms and phenyl groups.

Examples of these products include those in which R is chosen from $C_1$-$C_4$ lower alkyl radicals, such as methyl, and phenyl radicals.

Commercial products corresponding to these resins include, but are not limited to, the product sold under the name "DOW CORNING 593" and those sold under the names "SILICONE FLUID SS 4230 and SS 4267" by the company GENERAL ELECTRIC and which are silicones with a dimethyl/trimethylsiloxane structure.

Further examples include resins of the trimethylsiloxysilicate type sold, for instance, under the names X22-4914, X21-5034, and X21-5037 by the company SHIN-ETSU.

The organomodified silicones which may be used in accordance with the present disclosure include silicones as defined above and comprising, in their structure, at least one organofunctional group attached by means of a hydrocarbon-based group.

Suitable organomodified silicones include polyorganosiloxanes comprising:

polyethyleneoxy and/or polypropyleneoxy groups optionally comprising $C_6$-$C_{24}$ alkyl groups, such as the products called dimethicone-copolyol sold by the company DOW CORNING under the name DC 1248; the SILWET® L 722, L 7500, L 77, and L 711 oils from the company UNION CARBIDE; and the ($C_{12}$)alkyl methicone copolyol sold by the company DOW CORNING under the name Q2 5200;

substituted or unsubstituted amino groups, such as the products sold under the name GP 4 Silicone Fluid and GP 7100 by the company GENESEE and the products sold under the names Q2 8220 and DOW CORNING 929 and 939 by the company DOW CORNING. The substituted amino groups may include, for example, $C_1$-$C_4$ aminoalkyl groups;

quaternary ammonium groups, such as the products sold under the names ABILQUAT 3272 and ABILQUAT 3474 by the company GOLDSCHMIDT;

thiol groups, such as the products sold under the names "GP 72 A" and "GP 71" from GENESEE;

alkoxylated groups, such as the product sold under the name "SILICONE COPOLYMER F-755" by SWS SILICONES and ABIL WAX® 2428, 2434 and 2440 by the company GOLDSCHMIDT;

hydroxyl groups, such as the polyorganosiloxanes with a hydroxyalkyl function, described, for example, in French Patent Application No. 85 16334;

acyloxyalkyl groups such as the polyorganosiloxanes described in U.S. Pat. No. 4,957,732;

anionic groups of the carboxylic acid type such as in the products described in European Patent No. 0 186 507 from the company CHISSO CORPORATION, or of the alkylcarboxylic type such as those present in the product X-22-3701E from the company SHIN-ETSU; 2-hydroxyalkyl sulphonate; and 2-hydroxyalkyl thiosulphate, such as the products sold by the company GOLDSCHMIDT under the names "ABIL® S201" and "ABIL® S255"; and hydroxyacylamino groups, such as the polyorganosiloxanes described in European Patent Application No. 0 342 834, for example, the product Q2-8413 from the company DOW CORNING.

In one embodiment, the at least one silicone may be chosen from polydimethylsiloxanes such as polydimethylsiloxanes with trimethylsilyl end groups, polydimethylsiloxanes with hydroxydimethylsilyl end groups, and aminated silicones.

The at least one silicone may be present in the composition in an amount ranging from 0.05 to 20% by weight, for example, from 0.1 to 10% by weight, or from 0.5 to 5% by weight relative to the total weight of the composition.

The compositions according to the present disclosure may be in a form chosen from shower gels, shampoos, and compositions to be applied before or after a shampoo, the latter being in a form chosen from more or less thickened lotions, gels, and emulsions.

According to one embodiment, the composition also comprises at least one anti-dandruff agent, for example, piroctone olamine, zinc pyrithione, salicylic acid, selenium disulphide, and mixtures thereof.

The at least one anti-dandruff agent may be present in the composition in an amount ranging from 0.001 to 10% by weight, for example, from 0.1 to 5% by weight, or from 0.2 to 2% by weight, relative to the total weight of the composition.

The aqueous medium may be chosen from water and mixtures of water and at least one cosmetically acceptable solvent chosen from $C_1$-$C_4$ lower alcohols, such as ethanol, isopropanol, tert-butanol, and n-butanol; polyols such as glycerol, propylene glycol, and polyethylene glycols; and mixtures thereof.

The pH of the composition according to the present disclosure generally may be less than 8.5, for example, ranging from 4 to 7.

The composition according to the present disclosure may also comprise at least one conventional additive known in the art, such as anti-hairloss agents, oxidizing agents, ceramides, pseudoceramides, vitamins, provitamins, including panthenol, plant, animal, mineral, and synthetic oils, waxes, sunscreens, coloured or non-coloured, inorganic or organic pigments, dyes, pearlescent agents, opacifiers, sequestering agents, plasticizers, solublizing agents, acidifying agents, basifying agents, inorganic or organic thickeners, antioxidants, hydroxy acids, fragrances, and preserving agents.

Examples of opacifiers include, but are not limited to, compounds such as ethylene glycol distearate.

It is to be understood that a person skilled in the art will take care to select the at least one optional additive and the amount thereof in such a way that the properties of the compositions of the present disclosure are not, or are not substantially affected.

The at least one optional additives may be present in the composition in an amount ranging from 0 to 20% by weight relative to the total weight of the composition.

The composition according to the present disclosure may be used as a composition for the cosmetic treatment and/or care of the hair and/or skin. For instance, the composition may be used as a shampoo or a composition to be applied before or after a shampoo.

Also disclosed herein is a cosmetic treatment process comprising applying an effective amount of a composition of the present disclosure to the hair.

According to one embodiment, such a process comprises applying an effective amount of the cosmetic composition to the hair and rinsing it out after it has optionally been left on for a period of time.

When the composition according to the present disclosure is applied in the form of a lotion or a cream before or after shampooing, it is optionally left on the hair for approximately half a minute to 5 minutes, and then optionally rinsed out with water.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

In the following examples, all the amounts are indicated as percentage by weight of active material relative to the total weight of the composition, unless otherwise indicated.

Example 1

Two shampoo compositions, in accordance with the present disclosure, were prepared from the ingredients indicated in the table below.

Composition A is an anti-dandruff shampoo, whereas composition B is a shampoo for children.

| Composition | A | B |
|---|---|---|
| Sodium lauryl ether sulphate comprising 2.2 OE in aqueous solution (Texapon N702 from Cognis) | 9.9 | 7 |
| Cocoylamidopropylbetaine/glyceryl monolaurate in aqueous solution 25/75 (Tegobetaine HS from Goldschmidt) | 3.9 | — |
| Oxyethylene sorbitan monolaurate comprising 4 OE (Tween 21 from Uniqema) | 6 | 7 |
| 80/20 sodium magnesium lauryl ether sulphate comprising 4 OE, in aqueous solution at 52% (Texapon ASV 50 from Cognis) | 3.1 | 2.5 |
| Oxyethylene sorbitan monolaurate comprising 20 OE (Tween 20 from Uniqema) | 2 | 0.5 |
| Ethylene glycol distearate (Tegin BL 315 from Goldschmidt) | 1.5 | 1.5 |
| Sodium N-cocoylamidoethyl, N-ethoxycarboxymethyl glycinate (Miranol C2M conc from Rhodia) | 0.6 | 3.1 |
| Hexylene glycol (2 methyl-2,4 pentanediol) | 1 | 0.5 |
| Methacryloylethyl N,N-dimethyl carboxymethyl betaine/methyl methacrylate copolymer at 22% in water/ethanol 68/32 (Mexomere PX from Chimex) | 0.2 | 0.15 |
| Polyethylene glycol dioleate (55 OE) and propylene glycol dioleate in aqueous glycolic solution (NTIL 141 liquid from Goldschmidt) | 0.8 | |
| 1-Hydroxy-4-methyl-6-trimethylpentyl-2-pyridone, monoethanolamine salt (Octopirox from Clariant) | 0.5 | |
| Sodium benzoate | 0.5 | |
| Fragrance | 0.5 | 0.5 |
| Mixture of methyl, butyl, ethyl, propyl and isobutyl p-hydroxybenzoate (7/57/22/14) (Nipastat from Nipa) | 0.5 | |
| Guar hydroxypropyl trimethylammonium chloride (Jaguar C13S from Rhodia) | 0.25 | 0.17 |
| Powdered salicylic acid | 0.2 | |
| Carboxyvinyl polymer synthesized in an ethyl acetate/cyclohexane mixture (Carbopol 980 from Noveon) | 0.1 | 0.1 |
| Methyl p-hydroxybenzoate | 0.02 | 0.02 |
| 1,3-Dimethylol-5,5-dimethyl hydantoin in aqueous solution (Glydant LTD from Lonza) | | 0.14 |
| Methyl p-hydroxybenzoate, sodium salt (Nipagin M sodium from Clariant) | | 0.18 |
| Propylene glycol | 0.1 | 0.1 |
| Mixture of oxyethylenated palm (200 OE) and oxyethylenated coconut (7 OE) glycerides in aqueous suspension (Rewoderm LI-S80 from Goldschmidt) | | 1.20 |
| Water qs | 100% | 100% |

Compositions A and B in accordance with the present disclosure were found to exhibit an excellent tolerance with respect to the scalp. For instance, very few discomforting reactions were observed.

In addition, these compositions, for instance the children's shampoo of composition B, were extremely gentle and exhibited excellent ocular tolerance.

Finally, these compositions exhibited notable cosmetic properties of softness, disentangling, and smoothness of the hair, and of styling and volume.

Example 2

Comparative Tests

A shampoo composition C, according to the present disclosure, and a shampoo composition D, which does not comprise any surfactants in the form of magnesium salts, were prepared from the ingredients indicated in the table below.

| Composition | C | D |
|---|---|---|
| Sodium lauryl ether sulphate comprising 2.2 OE in aqueous solution (Texapon N702 from Cognis) | 7 | 10.5 |
| 80/20 sodium/magnesium lauryl ether sulphate comprising 4 OE, in aqueous solution at 52% (Texapon ASV 50 from Cognis) | 3.5 | |
| Sodium N-cocoylamidoethyl, N-ethoxycarboxymethyl glycinate (Miranol C2M conc from Rhodia) | 2.01 | 2.01 |
| Oxyethylene sorbitan monolaurate comprising 4 OE (Tween 21 from Uniqema) | 8 | 8 |
| Guar hydroxypropyltrimethylammonium chloride (Jaguar C13S from Rhodia) | 0.25 | 0.25 |
| Methacryloylethyl N,N-dimethylcarboxymethyl betaine/methyl methacrylate copolymer at 22% in water/ethanol 68/32 (Mexomere PX from Chimex) | 0.11 | 0.11 |
| Powdered salicylic acid | 0.2 | 0.2 |
| Preserving agents | 1 | 1 |
| Citric acid q.s. | pH 5.5 | pH 5.5 |
| Water qs | 100% | 100% |

Shampoo compositions C and D were each tested on 10 models. The results obtained were as follows:

For 90% of the models tested, composition C gave better visual smoothness compared with composition D, and for 70% of the models tested, the hair treated with composition C was more flexible and had a better feel compared with that treated with composition D.

Thus, composition C in accordance with the present disclosure was found to provide better cosmetic properties as compared with composition D. Moreover, at an equal total amount of anionic surfactant, the presence of an anionic surfactant in the form of a magnesium salt substantially improved the properties of the shampoo composition.

What is claimed is:

1. A cosmetic composition for washing keratin materials, comprising, in an aqueous medium:
    (a) at least 0.1% by weight relative to the total weight of the composition of at least a first anionic surfactant in the form of a magnesium salt selected from the group consisting of magnesium ($C_{12-24}$) alkyl ether sulphates comprising from 1 to 16 ethylene oxide units,
    (b) from 0.5% to 20% by weight relative to the total weight of the composition of at least a second anionic surfactant different from the first, selected from the group consisting of the sodium salts of polyoxyalkylenated ($C_{6-24}$ alkyl) ether carboxylic acids comprising from 2 to 50 ethylene oxide, units, the sodium salts of polyoxyalkylenated ($C_{6-24}$ alkyl)($C_{6-24}$ aryl) ether carboxylic acids comprising from 2 to 50 ethylene oxide units, the sodium salts of polyoxyalkylenated ($C_{6-24}$ alkyl) amido ether carboxylic acids comprising from 2 to 50 ethylene oxide units, the sodium salts of alkyl sulphates, and the sodium salts of alkylether sulphates,
    (c) from 0.5% to 8% by weight relative to the total weight of the composition of at least one amphoteric or zwitterionic surfactant selected from the group consisting of:
        (i) derivatives of secondary aliphatic amines and derivatives of tertiary aliphatic amines, in which the aliphatic groups are chosen from linear and branched chains comprising from 8 to 22 carbon atoms and containing at least one anionic carboxylate group; and
    (d) from 0.5% to 10% by weight relative to the total weight of the composition of at least one oxyethylenated sorbitan ester, and
    (e) from 0.1% to 5% by weight relative to the total weight of the composition of at least one polymer chosen from cationic polymers and amphoteric or zwitterionic polymers.

2. The composition according to claim 1, wherein the at least one first anionic surfactant is present in the composition in an amount ranging from 0.1% to 10% by weight relative to the total weight of the composition.

3. The composition according to claim 2, wherein the at least one first anionic surfactant is present in the composition in an amount ranging from 0.2% to 8% by weight relative to the total weight of the composition.

4. The composition according to claim 3, wherein the at least one first anionic surfactant is present in the composition in an amount ranging from 0.3% to 2% by weight relative to the total weight of the composition.

5. The composition according to claim 1, wherein the at least one second anionic surfactant is selected from the group consisting of the sodium salts of polyoxyalkylenated ($C_{6-24}$ alkyl) ether carboxylic acids comprising from 2 to 50 ethylene oxide units, the sodium salts of polyoxyalkylenated ($C_{6-24}$ alkyl)($C_{6-24}$ aryl) ether carboxylic acids comprising from 2 to 50 ethylene oxide units, and the sodium salts of polyoxyalkylenated ($C_{6-24}$ alkyl) amido ether carboxylic acids comprising from 2 to 50 ethylene oxide units.

6. The composition according to claim 1, wherein the at least one second anionic surfactant is selected from the group consisting of the sodium salts of alkyl sulphates and the sodium salts of alkyl ether sulphates.

7. The composition according to claim 1, wherein the at least one second anionic surfactant is present in the composition in an amount ranging from 1% to 20% by weight relative to the total weight of the composition.

8. The composition according to claim 7, wherein the at least one second anionic surfactant is present in the composition in an amount ranging from 3% to 15% by weight relative to the total weight of the composition.

9. The composition according to claim 1, wherein the at least one amphoteric or zwitterionic surfactant is present in the composition in an amount ranging from 1% to 8% by weight relative to the total weight of the composition.

10. The composition according to claim 1, wherein the at least one oxyethylenated sorbitan ester is selected from the group consisting of oxyethylenated derivatives of monoesters of $C_{8-30}$ fatty acids and of sorbitan comprising from 1 to 50 ethylene oxide units and oxyethylenated derivatives of polyesters of $C_{8-30}$ fatty acids and of sorbitan comprising from 1 to 50 ethylene oxide units.

11. The composition according to claim 10, wherein the at least one oxyethylenated sorbitan ester is selected from the group consisting of oxyethylenated derivatives of monoesters of $C_{12-24}$ fatty acids and of sorbitan comprising from 4 to 20 ethylene oxide units and oxyethylenated derivatives of monoesters and polyesters of $C_{12-24}$ fatty acids and of sorbitan comprising from 4 to 20 ethylene oxide units.

12. The composition according to claim 11, wherein the fatty acid of the at least one oxyethylenated sorbitan ester is a saturated fatty acid.

13. The composition according to claim 1, wherein the at least one oxyethylenated sorbitan ester is selected from the group consisting of oxyethylene sorbitan monolaurate comprising 4 ethylene oxide units and oxyethylene sorbitan monolaurate comprising 20 ethylene oxide units.

14. The composition according to claim 1, wherein the at least one oxyethylenated sorbitan ester is present in the composition in an amount ranging from 2 to 9% by weight relative to the total weight of the composition.

15. The composition according to claim 1, wherein the at least one polymer is selected from the group consisting of cationic polymers comprising at least one group chosen from primary amine groups, secondary amine groups, tertiary amine groups, and quaternary amine groups, wherein said at least one group may either be part of the main polymer chain or may be carried by a side substituent directly connected to the main chain.

16. The composition according to claim 15, wherein cationic polymers are selected from the group consisting of cellulose ether derivatives comprising quaternary ammonium groups, cationic cyclopolymers, guar gums modified with a 2,3-epoxypropyltrimethylammonium salt, and quaternary polymers of vinylpyrrolidone and of vinylimidazole.

17. The composition of claim 16, wherein the cationic cyclopolymers are chosen from dimethyldiallylammonium chloride homopolymers and copolymers.

18. The composition according to claim 1, wherein the at least one amphoteric or zwitterionic polymer is selected from the group consisting of polymers comprising K and M units distributed randomly in the polymer chain, wherein:

K is chosen from units derived from a monomer comprising at least one basic nitrogen atom and M is selected from the group consisting of units derived from an acidic monomer comprising at least one group selected from the group consisting of carboxylic and sulphonic groups, or K and M are selected from the group consisting of groups derived from zwitterionic monomers of carboxybetaines or of sulphobetaines, or K and M are selected from the group consisting of cationic polymer chains comprising at least one group selected from the group consisting of primary, secondary, tertiary, and quaternary amine groups, wherein at least one of the amine groups bears a selected from the group consisting of carboxylic and sulphonic groups connected via a hydrocarbon-based radical, or K and M are part of a chain of a polymer comprising an α,β-dicarboxylic ethylene unit in which one of the carboxylic groups has been reacted with a polyamine comprising at least one group selected from the group consisting of primary and secondary amine groups.

19. The composition according to claim 18, wherein the at least one amphoteric or zwitterionic polymer is a polymer resulting from the copolymerization of a monomer derived from a vinyl compound bearing a carboxylic group, selected from the group consisting of acrylic acid, methacrylic acid, maleic acid, and alpha-chloroacrylic acid, and of a basic monomer derived from a substituted vinyl compound comprising at least one basic atom.

20. The composition according to claim 1, comprising at least two different polymers, selected from the group consisting of cationic polymers and amphoteric or zwitterionic polymers.

21. The composition according to claim 1, comprising at least one cationic polymer and at least one amphoteric or zwitterionic polymer.

22. The composition according to claim 1, further comprising at least one anti-dandruff agent.

23. The composition according to claim 22, wherein the at least one anti-dandruff agent is selected from the group consisting of piroctone olamine, zinc pyrithione, salicylic acid, and selenium disulphide.

24. The composition according to claim 22, wherein the at least one anti-dandruff agent is present in the composition in an amount ranging from 0.001% to 10% by weight relative to the total weight of the composition.

25. The composition according to claim 24, wherein the at least one anti-dandruff agent is present in the composition in an amount ranging from 0.1% to 5% by weight relative to the total weight of the composition.

26. The composition according to claim 1, further comprising at least one silicone.

27. The composition according to claim 1, wherein the aqueous medium is selected from the group consisting of water and mixtures of water and at least one cosmetically acceptable solvent.

28. The composition according to claim 27, wherein the at least one solvent is selected from the group consisting of $C_1$-$C_4$ lower alcohols and polyols.

29. The composition according to claim 1, further comprising at least one additive selected from the group consisting of anti-hairloss agents, oxidizing agents, ceramides, pseudoceramides, vitamins, provitamins, panthenol, plant, animal, mineral, or synthetic oils, waxes, sunscreens, coloured or non-coloured, inorganic or organic pigments, dyes, pearlescent agents, opacifiers, sequestrants, plasticizers, solubilizing agents, acidifying agents, basifying agents, inorganic or organic thickeners, antioxidants, hydroxy acids, fragrances, and preserving agents.

30. The composition according to claim 1, wherein the composition is in a form selected from the group consisting of shampoos and compositions to be applied before or after a shampoo.

31. A cosmetic hair treatment process, comprising applying an effective amount of the composition of claim 1 to the hair.

32. The composition according to claim 1, wherein the at least one first anionic surfactant is magnesium lauryl ether sulphate.

* * * * *